(12) United States Patent
Caffrey et al.

(10) Patent No.: US 9,914,954 B1
(45) Date of Patent: *Mar. 13, 2018

(54) METHOD FOR MEASUREMENT OF BIOAVAILABLE TESTOSTERONE

(71) Applicant: Naviga LLC, Virginia Beach, VA (US)

(72) Inventors: Rebecca Caffrey, Chesterfield, VA (US); Daniel Hoefner, Ashland, VA (US)

(73) Assignee: NAVIGA LLC, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/276,994

(22) Filed: Sep. 27, 2016

Related U.S. Application Data

(63) Continuation-in-part of application No. 14/661,306, filed on Mar. 18, 2015, now Pat. No. 9,482,678.

(60) Provisional application No. 61/954,968, filed on Mar. 18, 2014.

(51) Int. Cl.
*C12Q 1/26* (2006.01)

(52) U.S. Cl.
CPC ......... *C12Q 1/26* (2013.01); *G01N 2333/575* (2013.01); *G01N 2333/90245* (2013.01)

(58) Field of Classification Search
None
See application file for complete search history.

(56) References Cited

U.S. PATENT DOCUMENTS 9,482,678 B1 * 11/2016 Caffrey ................ G01N 33/743

* cited by examiner

*Primary Examiner* — Lisa V Cook
(74) *Attorney, Agent, or Firm* — Whitham, Curtis & Cook

(57) ABSTRACT

Provided are methods for determining level of bioactive testosterone in a biological sample. In one aspect, aromatase enzyme is utilized to convert free, bio-available testosterone into estradiol and the amount of estradiol is measured before and after the addition of enzyme. The difference in measurements provides the amount of bioactive testosterone in the sample. In another aspect, a competitor of testosterone binding to SHBG is utilized to displace testosterone bound to SHBG. Measurements of total testosterone in the sample before addition of competitor and afterwards are taken, such that the delta reflects the amount of testosterone that was bound on SHBG.

4 Claims, 3 Drawing Sheets

METHOD FOR MEASUREMENT OF BIOAVAILABLE TESTOSTERONE

CROSS REFERENCE TO RELATED APPLICATIONS

This application is a continuation in part of U.S. Ser. No. 14/661,306 filed Mar. 18, 2015, now U.S. Pat. No. 9,482,678, and claims priority to U.S. Provisional application 61/954,968 filed on Mar. 18, 2014.

FIELD OF THE INVENTION

Embodiments of the invention relate to accurate and sensitive techniques for determining a level of bioactive testosterone in a biological sample.

BACKGROUND OF THE INVENTION

Testosterone is the major androgenic hormone. It is responsible for the development of the male external genitalia and secondary sexual characteristics. In females, its main role is as an estrogen precursor. In both genders, it also exerts anabolic effects and influences behavior.

In men, testosterone is secreted by the testicular Leydig cells and, to a minor extent, by the adrenal cortex. In premenopausal women, the ovaries are the main source of testosterone with minor contributions by the adrenals and peripheral tissues. After menopause, ovarian testosterone production is significantly diminished. Testosterone production in testes and ovaries is regulated via pituitary-gonadal feedback involving luteinizing hormone (LH) and, to a lesser degree, inhibins and activins.

Most circulating testosterone is bound to sex hormone-binding globulin (SHBG), which in men also is called testosterone-binding globulin. A lesser fraction is albumin bound and a small proportion exists as free hormone. Historically, only the free testosterone was thought to be the biologically active component. However, testosterone is weakly bound to serum albumin and dissociates freely in the capillary bed, thereby becoming readily available for tissue uptake. All non-SHBG-bound testosterone is therefore considered bioavailable.

During childhood, excessive production of testosterone induces premature puberty in boys and masculinization in girls. In adult women, excess testosterone production results in varying degrees of virilization, including hirsutism, acne, oligo-amenorrhea, or infertility. Mild-to-moderate testosterone elevations are usually asymptomatic in males, but can cause distressing symptoms in females. The exact causes for mild-to-moderate elevations in testosterone often remain obscure. Common causes of pronounced elevations of testosterone include genetic conditions (eg, congenital adrenal hyperplasia); adrenal, testicular, and ovarian tumors; and abuse of testosterone or gonadotrophins by athletes.

Decreased testosterone in females causes subtle symptoms. These may include some decline in libido and non-specific mood changes. In males, it results in partial or complete degrees of hypogonadism. This is characterized by changes in male secondary sexual characteristics and reproductive function. The cause is either primary or secondary/tertiary (pituitary/hypothalamic) testicular failure. In adult men, there also is a gradual modest, but progressive, decline in testosterone production starting between the 4th and 6th decades of life. Since this is associated with a simultaneous increase of SHBG levels, bioavailable testosterone may decline more significantly than apparent total testosterone, causing nonspecific symptoms similar to those observed in testosterone deficient females. However, severe hypogonadism, consequent to aging alone, is rare.

Current methods for measuring free testosterone in biological fluid such as blood rely on measuring total testosterone, then measuring the amount of Sex Hormone Binding Globulin (SHBG) which binds the testosterone which is not free, and in some cases also measuring albumin (since testosterone can be bound by this as well), and then calculating an approximate amount of free testosterone by subtracting the amount theoretically bound to SHBG and the amount theoretically bound to albumin from the total measured testosterone. SHBG binds other sex hormones besides testosterone, so the assumption that the amount of SHBG equals the amount of bound testosterone is not accurate. This is also true for albumin which binds thousands of ligands non-specifically. This process is laborious, inaccurate, not reproducible with repeat measurements (high CVs), and requires the extra steps of measuring SHBG levels and albumin solely for the purpose of estimating how much of the total testosterone is free, which is presumed to be bio-available or bio-active. However, even if this method were to accurately measure the free testosterone, which it doesn't, free testosterone is not equivalent to bio-active testosterone when various cell reporter assays for bio-activity are used. Cell-based reporter assays are not suitable for clinical diagnostic use although they are useful as validation testing to demonstrate that a given assay such as described herein accurately measures bioavailable bioactive testosterone.

Measurement of total testosterone is often sufficient for diagnosis of morbidities or abnormalities, particularly if it is combined with measurements of LH and follicle-stimulating hormone (FSH). However, these tests are insufficient for diagnosis of mild abnormalities of testosterone homeostasis, particularly if abnormalities in SHBG function or levels are present. Therefore, additional methods for the measurements of free testosterone or bioavailable testosterone are needed in the art.

SUMMARY OF THE INVENTION

Biologically active testosterone and free testosterone are not necessarily the same even though some researchers and clinicians use the terms interchangably. The term "free testosterone" or "free T" refers simply to testosterone which is unbound by proteins in the bloodstream. The two proteins that are known to bind testosterone in the blood and are sometimes measured and used in calculating the approximate amount of free testosterone are SHBG and albumin. However, testosterone may be bound up by other proteins as well. Biological activity of testosterone, however, may be affected by other variables besides the binding of these proteins. Other chemical entities such as medications, supplements, ingested food compounds or other hormones with biological activity may bind to testosterone, act to inhibit the free testosterone, or compete with the free testosterone for the aromatase enzyme. Thus, the "free T" defined as unbound by SHBG and albumin may not be available to induce biological effects. Researchers have used in vivo cell-based assays to quantify bioavailable testosterone; generally, a cell type that is stimulated to activity or growth by testosterone is exposed to a sample of patient serum and the cell's activation or growth is measured by uptake of various substances (i.e. tritiated thymidine, BRDU) or cell counts are done to quantify the relative amount of biologically available testosterone. Other researchers have attempted to design systems wherein a quantifiable product like GFP is produced by transfected cells when those cells are exposed to testosterone. However, these systems are not conducive to rapid measurement in a diagnostic lab, are biologically "noisy" due to the reliance on live cell culture, are expensive and time-consuming to perform, are only semi-quantitative, and suffer from lack of reproducibility.

Embodiments of the invention described herein include measuring the sum total of a patient's biologically active testosterone, regardless of what protein or chemical entity is binding to it or inhibiting it or competing with it, because this assay utilizes the enzyme aromatase to measure the biological activity. Any testosterone in the patient's serum that binds to aromatase will be aromatized, or converted, to estradiol. Therefore, addition of exogenous aromatase to a patient sample and measurement of the change in estradiol amounts is an absolute quantification of the amount of testosterone that is biologically available as a ligand to bind to that enzyme. Thus, this assay most closely approximates measurements of biological activity of testosterone performed in vivo in cell-based systems, and does so in a rapid and accurate way that can be quantified in absolute terms by comparison to positive and negative controls and standard calibrant techniques.

Embodiments of the invention include a novel method of measuring bioactive testosterone that is more accurate than existing laboratory methods. In one embodiment, aromatase enzyme is utilized to convert free, bio-available testosterone into estradiol. The amount of estradiol in a sample is measured before addition of aromatase and after, as the delta reflects the amount of bio-available testosterone in the sample. In another embodiment, a competitor is utilized to displace testosterone bound to SHBG, with one measurement of total testosterone in the sample before addition of competitor and one measurement afterwards, such that the delta reflects the amount of testosterone that was bound on SHBG. Exemplary competitors include xenoestrogens and phytoestrogens. In an additional embodiment, using the methods described herein, the value measured for bound testosterone is added to the value measured for free/bioactive testosterone and the sum of the measurements would approximate the measured total testosterone, providing an internal control.

Some embodiments of the invention include a method for measuring or determining a level of biologically active testosterone in a biological sample of a subject comprising
converting testosterone in said sample to a testosterone precursor by exposure of said sample to amoratase enzyme;
detecting either said testosterone or said testosterone precursor in said sample before and after said converting step; and
calculating biologically active testosterone in said sample from differences between either said testosterone or said testosterone precursor detected before and after said converting step.

An example of these embodiments of the invention provide an indirect method for measuring or determining a level of one or more biologically active compounds in a biological sample of a subject, comprising:
 a) measuring a first concentration of estradiol ($E2_1$) in the biological sample;
 b) adding an aromatase enzyme and a NADPH cofactor to the biological sample to facilitate an aromatase reaction with the testosterone;
 c) measuring a second concentration of estradiol ($E2_2$) after the aromatase reaction; and then
 d) determining a level of biologically available testosterone in the biological sample of the subject,
wherein the level of biologically available testosterone includes calculating the difference between the second concentration of estradiol ($E2_2$) and the first concentration of estradiol ($E2_1$).

Another example of these embodiments provide method for measuring or determining a level of biologically active testosterone in a biological sample of a subject, comprising:
 a) obtaining a first measurement of total testosterone for the biological sample; then
 b) adding an aromatase enzyme and a NADPH cofactor to the biological sample to facilitate an aromatase reaction with testosterone in the biological sample; then
 c) obtaining a second measurement of total testosterone for the biological sample after the aromatase reaction; and then
 d) calculating the level of the biologically active testosterone in the sample based on the difference between the first measurement and the second measurement of total testosterone.

In some embodiments, the method further comprises the steps of
 e) adding a competitive sex hormone binding globulin (SHBG) ligand to displace or dissociate testosterone from SHBG;
 f) measuring a second level of biologically active testosterone in the biological sample; and
 g) determining a level of SHBG that was bound to testosterone in the biological sample,
wherein the level of SHBG includes calculating the difference between the concentration of biologically active testosterone measured before and after the addition of the competitive SHGB ligand.

In some embodiments, the one or more of steps of measuring are performed by
immobilizing a labeled probe specific for binding to said estradiol on a solid surface;
contacting immobilized labeled probe with said estradiol; and
detecting an estradiol-probe complex.

Is some aspects, the biological sample is serum, plasma or saliva. In some embodiments, the first concentration of estradiol ($E2_1$) and the second concentration of estradiol ($E2_2$) are measured by electrochemiluminescence immunoassay (ECLIA).

Further embodiments of the invention provide a method for determining a level of sex hormone binding globulin (SHBG)-bound testosterone (SHBG-T) in a biological sample of a subject, comprising:
 a) measuring a first concentration of total testosterone ($TT_1$) in the biological sample;
 b) adding a competitive SHBG ligand to displace or dissociate testosterone from the SHBG;
 c) measuring a second concentration of total testosterone ($TT_2$) in the biological sample after the competitive SHBG ligand addition; and then
 d) calculating the level of SHBG-bound testosterone (SHBG-T) in the biological sample of the subject based on the measurement in (c),
wherein the level of sex hormone binding globulin (SHBG)-bound testosterone (SHBG-T) includes calculating the difference between the second concentration of total testosterone ($TT_2$) and the first concentration of total testosterone ($TT_1$).

In some embodiments, the total testosterone (TT) includes SHBG-bound testosterone (SHBG-T), free testosterone (FT)

and non-SHBG, albumin-bound testosterone (non-SHBG-AT). In some embodiments, the level of total testosterone (TT) is measured using a technique selected from the group consisting of enzyme-linked immunosorbent assay (ELISA), radioimmunoassay, mass spectrometry, liquid chromatography-tandem mass spectrometry (LC-MS/MS), and electrochemiluminescence or electrogenerated chemiluminescence (ECL).

In some embodiments, the binding affinity for the competitive SHBG ligand ranges from about $0.02 \times 10^5$ to about $7.8 \times 10^5$ L/M. The competitive SHBG ligand can be a phytoestrogen or a xenoestrogen. Exemplary phytoestrogens include, but are not limited to, isoflavones, lignins, and coumestans. Exemplary xenoestrogens include, but are not limited to 17β-estradiol, genistein, bisphenol A, resorcinol monobenzoate and phenyl salicylate.

In some embodiments, the methods of the invention further comprise determining a molar ratio of SHBG-bound testosterone (SHBG-T) to SHBG in the biological sample, wherein said molar ratio is calculated by dividing the level of sex hormone binding globulin (SHBG)-bound testosterone (SHBG-T) expressed in a molar concentration and as obtained in (d) with a known molar concentration of competitive SHBG ligand as added in (b).

Other aspects of the invention provide a method for determining a level of non-SHBG, albumin-bound testosterone (non-SHBG-AT) in a biological sample of a subject, comprising:
  a) measuring a first concentration of total testosterone ($TT_1$) in the biological sample;
  b) adding a competitive SHBG ligand to the biological sample to effect displacement or dissociation of testosterone from the SHBG;
  c) measuring a second concentration of total testosterone ($TT_2$) in the biological sample;
  d) calculating a level of SHBG-bound testosterone (SHBG-T) in the biological sample of the subject based on the measurement in (c);
  e) measuring a first concentration of estradiol ($E2_1$);
  f) adding an aromatase enzyme and a NADPH cofactor to the biological sample to facilitate an aromatase reaction with the testosterone;
  g) measuring a second concentration of estradiol ($E2_2$) after the aromatase reaction;
  h) determining a level of free testosterone (FT) in the biological sample of the subject based on the measurement in (g); and then
  i) calculating a level of non-SHBG, albumin-bound testosterone (non-SHBG-AT) based on the measurements in (d) and (h),
  wherein the level of non-SHBG, albumin-bound testosterone (non-SHBG-AT) includes subtracting the levels of SHBG-bound testosterone (SHBG-T) in (d) and free testosterone (FT) in (h) from the level of first concentration of total testosterone ($TT_1$) in (a). This method may further comprise:
  j) summing up the calculated levels of SHBG-bound testosterone (SHBG-T) of
  (d), free testosterone (FT) of (h) and non-SHBG, albumin-bound testosterone (non-SHBG-AT) of (i), wherein the sum is the approximated total testosterone level.

Other aspects of the invention provide a kit comprising a blood card and optionally directions, a lancet, and/or a pre-paid mailing envelope, wherein the blood card comprises one spot that is impregnated with aromatase and/or aromatase and a NADPH cofactor.

Further aspects of the invention provide methods for treatment of testosterone-related disorders. Embodiments of the invention provide a method for treatment of a testosterone-related disorder in a subject, comprising:
  a) measuring a first concentration of estradiol ($E2_1$) in a biological sample;
  b) adding an aromatase enzyme and a NADPH cofactor to the biological sample to facilitate an aromatase reaction with the testosterone;
  c) measuring a second concentration of estradiol ($E2_2$) after the aromatase reaction; and then
  d) determining the level of free testosterone (FT) in the biological sample of the subject,
  wherein the level of free testosterone (FT) includes calculating the difference between the second concentration of estradiol ($E2_2$) and the first concentration of estradiol ($E2_1$), and
  e) administering to the subject a therapeutically effective amount of testosterone if the level of free testosterone (FT) is low, or administering to the subject a therapeutically effective amount of an agent that blocks testosterone if the level of free testosterone (FT) is high.

Embodiments of the invention provide a method for treatment of a testosterone-related disorder in a subject, comprising
  a) measuring a first concentration of total testosterone ($TT_1$) in the biological sample;
  b) adding a competitive SHBG ligand to displace or dissociate testosterone from the SHBG;
  c) measuring a second concentration of total testosterone ($TT_2$) in the biological sample after the competitive SHBG ligand addition; and then
  d) calculating the level of SHBG-bound testosterone (SHBG-T) in the biological sample of the subject based on the measurement in (c),
  wherein the level of sex hormone binding globulin (SHBG)-bound testosterone (SHBG-T) includes calculating the difference between the second concentration of total testosterone ($TT_2$) and the first concentration of total testosterone ($TT_1$), and
  e) administering to the subject a therapeutically effective amount of testosterone if the level of (SHBG)-bound testosterone (SHBG-T) is high, or administering to the subject a therapeutically effective amount of an agent that blocks testosterone if the level of (SHBG)-bound testosterone (SHBG-T) is low.

Embodiments of the invention provide a method for treatment of a testosterone-related disorder in a subject, comprising:
  a) measuring a first concentration of total testosterone ($TT_1$) in the biological sample;
  b) adding a competitive SHBG ligand to the biological sample to effect displacement or dissociation of testosterone from the SHBG;
  c) measuring a second concentration of total testosterone ($TT_2$) in the biological sample;
  d) calculating a level of SHBG-bound testosterone (SHBG-T) in the biological sample of the subject based on the measurement in (c);
  e) measuring a first concentration of estradiol ($E2_1$);
  f) adding an aromatase enzyme and a NADPH cofactor to the biological sample to facilitate an aromatase reaction with the testosterone;
  g) measuring a second concentration of estradiol ($E2_2$) after the aromatase reaction;

h) determining a level of free testosterone (FT) in the biological sample of the subject based on the measurement in (g); and then i) calculating a level of non-SHBG, albumin-bound testosterone (non-SHBG-AT) based on the measurements in (d) and (h), wherein the level of non-SHBG, albumin-bound testosterone (non-SHBG-AT) includes subtracting the levels of SHBG-bound testosterone (SHBG-T) in (d) and free testosterone (FT) in (h) from the level of first concentration of total testosterone ($TT_1$) in (a), and j) administering to the subject a therapeutically effective amount of testosterone if the level of non-SHBG, albumin-bound testosterone (non-SHBG-AT) is high, or administering to the subject a therapeutically effective amount of an agent that blocks testosterone if the level of non-SHBG, albumin-bound testosterone (non-SHBG-AT) is low.

DETAILED DESCRIPTION OF THE INVENTION

Figure 1:
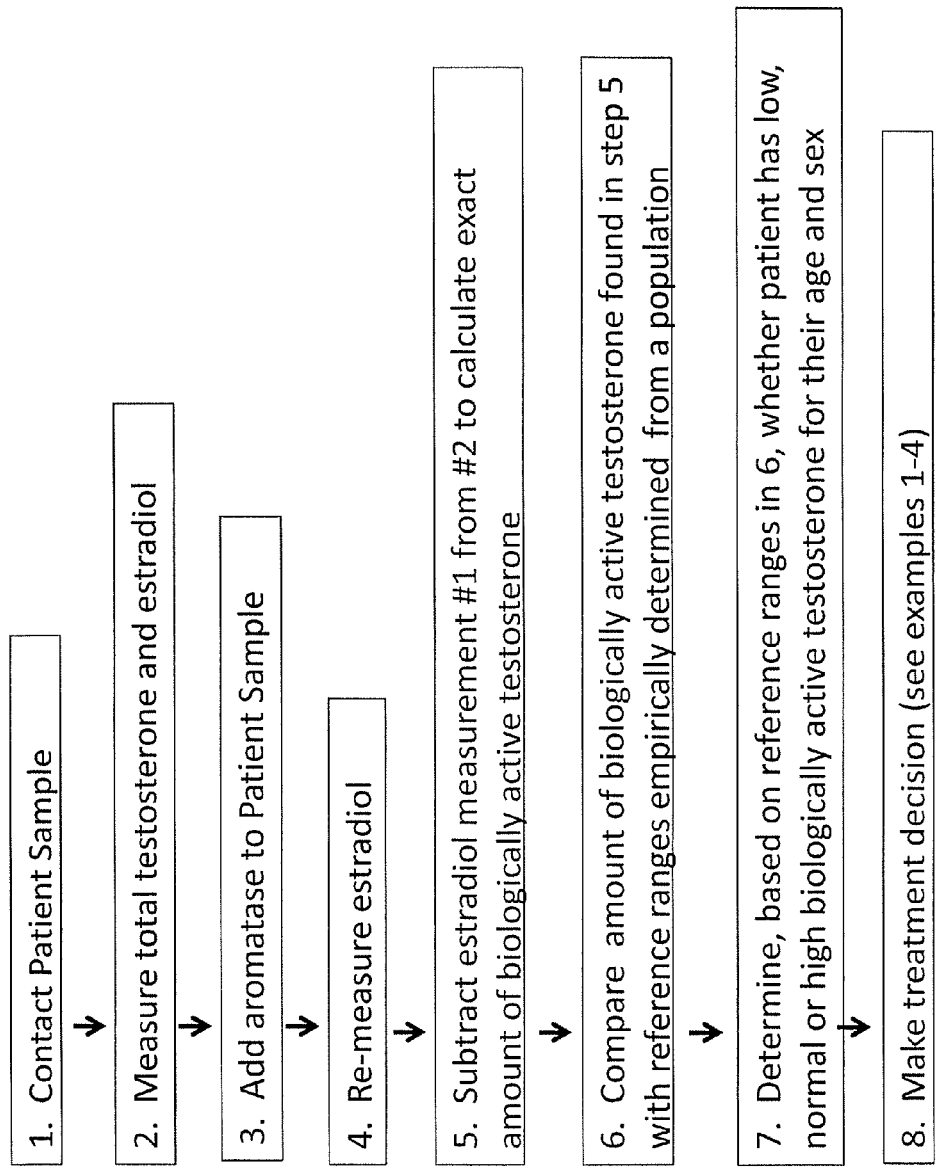
FIG. 1. Flow chart illustrating an exemplary embodiment of the invention.

Many have sought a better way to measure free and/or bioavailable testosterone in serum and this is notoriously difficult to do since testosterone is frequently bound to other proteins and receptors. Thus it is difficult for clinicians to accurately tell if a patient has a normal, high or low amount of unbound and bioavailable testosterone in their bloodstream.

Rather than attempting to catch testosterone with antibodies or receptors or precipitating total testosterone, aspects of the present invention exploit the biological function of the aromatase enzyme. The aromatase enzyme is normally present in tissue and converts testosterone to estradiol. Estradiol can be measured accurately and rapidly with an existing high-throughput clinical assay for hormones. It is an object of the invention to obtain the total testosterone in a sample, measure the amount of estradiol present at baseline, then run a reaction with whole serum/plasma with aromatase and NADPH cofactor added in. The amount of estradiol generated from free testosterone precursor is measured, the native baseline amount is subtracted, and the difference gives the amount of free testosterone. No calculations based on SHBG are needed because it would not matter what binding proteins (e.g. SHBG, albumin) were binding up the testosterone.

In some embodiments, an aromatase enzyme is used to convert testosterone to estradiol. In other embodiments, lipid carriers of aromatase and fragments of aromatase proteins and/or small molecule organics can also catalyze the same reaction. Some areas of aromatase are lipophilic and in some embodiments of the invention, the whole aromatase enzyme is bound in an artificial lipid "membrane" (e.g. micelles). The aromatase enzyme, lipid membranes containing aromatase, or other small molecule organics that catalyze the reaction can be added to the biological sample to catalyze the reaction in solution or bound to a solid support. Exemplary solid supports include, but are not limited to, a blood card surface, beads, film, etc. Reverse phase surfaced solid supports may also be used wherein the aromatase binds hydrophobically. In some embodiments, aromatase is bound to beads containing ferromagnetic material (metals) in an carrier (see U.S. Pat. No. 5,691,208, U.S. Pat. No. 5,705,059, and U.S. Pat. No. 5,711,871 incorporated herein by reference). Thus the beads are recovered and recycled by magnetic separation.

In additional embodiments, SHBG bound testosterone may be quantified in addition to free testosterone, thereby facilitating analysis of testosterone metabolism and its clinical ramifications. There are competitive ligands for SHBG that displace testosterone. These ligands include, but are not limited to, Xenoestrogens (various chemicals known to bind and disrupt interaction of SHBG and testosterone) and also some phytoestrogens. They have binding affinities ranging from 0.02 to 7.8 10(5) 1×mol(−1). These ligands displace testosterone from SHBG in human serum in a dose-dependent manner.

By mixing xenoestrogens with the higher binding affinities into serum containing SHBG-bound testosterone, the amount of testosterone released from SHBG can be measured. The amount of total testosterone, bound testosterone released from SHBG (presumed bioactive), and the amount of free testosterone in serum via the aromatase/estradiol method can then be measured. Adding the last two testosterone populations together (bound and free) results in a number very close to the total testosterone. If the measured testosterone level is less than the total testosterone, then the difference is the amount bound to other binding proteins such as albumin. Ratios of SHBG-bound testosterone to free testosterone and/or total testosterone, or any combination thereof can be correlated to risks of disease. These clinically significant and useful values and ratios are furthermore relevant to risk calculations for diabetes, cardiodiabetes, metabolic syndrome, fatty liver disease and cardiovascular health.

In combination with a SHBG-detection assay, a calculation of molar ratio of bound testosterone to SHBG present can be performed. If the SHBG is carrying less testosterone than is found to be within a range detected from a control population, additional testing or treatment can be carried out for the corresponding patient. Control populations may be used for the generation of normal ranges or ranges established in the prior art may be compared for generating risk levels, diagnosing disease, or detecting abnormalities. FIG. 1 illustrates an exemplary embodiment of the invention.

In particular embodiments, the invention provides a method for measuring or determining a level of one or more biologically active compounds in a biological sample of a subject, comprising:

a. measuring a first concentration of estradiol ($E2_1$) in the biological sample;

b. adding an aromatase enzyme and a NADPH cofactor to the biological sample to facilitate an aromatase reaction with the testosterone;

c. measuring a second concentration of estradiol ($E2_2$) after the aromatase reaction; and d. determining a level of biologically available testosterone in the biological sample of the subject, wherein the level of biologically available testosterone involves calculating the difference between the second concentration of estradiol ($E2_2$) and the first concentration of estradiol ($E2_1$).

In other embodiments for measuring or determining a level of biologically active testosterone in a biological sample of a subject, the following is performed:

a) obtaining a first measurement of total testosterone for the biological sample; then b) adding an aromatase enzyme and a NADPH cofactor to the biological sample to facilitate an aromatase reaction with testosterone in the biological sample; then c) obtaining a second measurement of total testosterone for the biological sample after the aromatase reaction; and then d) calculating the level of the biologically active testosterone in the sample based on the difference between the first measurement and the second measurement of total testosterone.

These embodiments basically involve a method for measuring or determining a level of biologically active testosterone in a biological sample of a subject comprising converting testosterone in said sample to a testosterone precursor by exposure of said sample to amoratase enzyme;

detecting either said testosterone or said testosterone precursor in said sample before and after said converting step; and calculating biologically active testosterone in said sample from differences between either said testosterone or said testosterone precursor detected before and after said converting step.

In some embodiments, the method further comprises the steps of e) adding a competitive sex hormone binding globulin (SHBG) ligand to displace or dissociate testosterone from SHBG;

f) measuring a second level of biologically active testosterone in the biological sample; and g) determining a level of SHBG that was bound to testosterone in the biological sample, wherein the level of SHBG includes calculating the difference between the concentration of biologically active testosterone measured before and after the addition of the competitive SHGB ligand.

In some embodiments, said steps of measuring are performed by immobilizing a labeled probe specific for binding to said estradiol on a solid surface;

contacting immobilized labeled probe with said estradiol; and detecting an estradiol-probe complex.

In preferred embodiments, the aromatase enzyme converts the free testosterone (FT) within the biological sample to estradiol (E2). In some embodiments, the biological sample is serum, plasma or saliva. In exemplary embodiments, the first concentration of estradiol ($E2_1$) and the second concentration of estradiol ($E2_2$) are measured by electrochemiluminescence immunoassay (ECLIA).

Additional aspects of the invention provide a method for determining a level of sex hormone binding globulin (SHBG)-bound testosterone (SHBG-T) in a biological sample of a subject, comprising:

a. measuring a first concentration of total testosterone ($TT_1$) in the biological sample;

b. adding a competitive SHBG ligand to displace or dissociate testosterone from the SHBG;

c. measuring a second concentration of total testosterone ($TT_2$) in the biological sample after the competitive SHBG ligand addition; and d. calculating the level of SHBG-bound testosterone (SHBG-T) in the biological sample of the subject based on the measurement in (c), wherein the level of sex hormone binding globulin (SHBG)-bound testosterone (SHBG-T) involves calculating the difference between the second concentration of total testosterone ($TT_2$) and the first concentration of total testosterone ($TT_1$), and In some embodiments, said steps of measuring are performed by immobilizing a labeled probe specific for binding to said testosterone on a solid surface;

contacting immobilized labeled probe with said testosterone; and detecting a testosterone-probe complex.

In some embodiments, the total testosterone (TT) includes SHBG-bound testosterone (SHBG-T), free testosterone (FT) and non-SHBG, albumin-bound testosterone (non-SHBG-AT). The level of total testosterone (TT) can be measured using a technique selected from the group consisting of enzyme-linked immunosorbent assay (ELISA), radioimmunoassay, mass spectrometry, liquid chromatography-tandem mass spectrometry (LC-MS/MS), and electrochemiluminescence or electrogenerated chemiluminescence (ECL). In some embodiments, the binding affinity for the competitive SHBG ligand ranges from about $0.02 \times 10^5$ to about $7.8 \times 10^5$ L/M.

In some embodiments, the competitive SHBG ligand is a phytoestrogen or a xenoestrogen. In exemplary embodiments, phytoestrogen is selected from the group consisting of isoflavones, lignins, and coumestans. In exemplary embodiments, xenoestrogen is selected from the group consisting of 17β-estradiol, genistein, bisphenol A, resorcinol monobenzoate and phenyl salicylate. In some aspects, a molar ratio of SHBG-bound testosterone (SHBG-T) to SHBG in the biological sample is determined, wherein said molar ratio is calculated by dividing the level of sex hormone binding globulin (SHBG)-bound testosterone (SHBG-T) expressed in a molar concentration and as obtained in (d) with a known molar concentration of competitive SHBG ligand as added in (b).

Aspects of the invention also provide a method for determining a level of non-SHBG, albumin-bound testosterone (non-SHBG-AT) in a biological sample of a subject, comprising:

a. measuring a first concentration of total testosterone ($TT_1$) in the biological sample;

b. adding a competitive SHBG ligand to the biological sample to effect displacement or dissociation of testosterone from the SHBG;

c. measuring a second concentration of total testosterone ($TT_2$) in the biological sample;

d. calculating a level of SHBG-bound testosterone (SHBG-T) in the biological sample of the subject based on the measurement in (c);

e. measuring a first concentration of estradiol ($E2_1$);

f. adding an aromatase enzyme and a NADPH cofactor to the biological sample to facilitate an aromatase reaction with the testosterone;

g. measuring a second concentration of estradiol ($E2_2$) after the aromatase reaction;

h. determining a level of free testosterone (FT) in the biological sample of the subject based on the measurement in (g); and i. calculating a level of non-SHBG, albumin-bound testosterone (non-SHBG-AT) based on the measurements in (d) and (h), wherein the level of non-SHBG, albumin-bound testosterone (non-SHBG-AT) involves subtracting the levels of SHBG-bound testosterone (SHBG-T) in (d) and free testosterone (FT) in (h) from the level of first concentration of total testosterone ($TT_1$) in (a), and In some embodiments, said steps of measuring are performed by
    immobilizing a labeled probe specific for binding to said testosterone or estradiol on a solid surface;
    contacting immobilized labeled probe with said testosterone or estradiol; and
    detecting a testosterone-probe or estradiol-probe complex.

In some embodiments, the above method further comprises summing up the calculated levels of SHBG-bound testosterone (SHBG-T) of (d), free testosterone (FT) of (h) and non-SHBG, albumin-bound testosterone (non-SHBG-AT) of (i), wherein the sum is the approximated total testosterone level.

The use of aromatase for the conversion of testosterone to estradiol for the purposes of measuring testosterone levels is a new feature to a standard aromatase assay. This method facilitates the measurement of free testosterone, which has different metabolic consequences than other forms of testosterone in vivo.

The use of SBHG ligands competitive to testosterone is a new feature for the measurement of testosterone in a subject. No other method exists that can rapidly measure the SHBG-bound portion of testosterone in the blood.

The calculation of different forms and conditions of testosterone in a subject (free vs. bound vs. bioavailable) is a new feature for the analysis of testosterone in human health and disease. The use of novel ratios of such forms/conditions of testosterone is a new feature for the reporting of testosterone in the context of human health and disease.

The methods described herein are more accurate and more reproducible than current methods of testosterone measurement. Furthermore the methods described herein relieve the need for measurement of proteins in the blood like albumin and SHBG, which add cost and complexity to clinical diagnostic methods.

Biological sample refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue).

As used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker, which may include a cleavage site) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator.

The term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

Estradiol can be measured with an Electrochemiluminescence Immunoassay "ECLIA"-Competition Assay. Assays can be set up using any technology known to those familiar with the art, and measurement of testosterone can similarly be accomplished after the various steps with any technology known to those in the art. The level of testosterone may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation; liquid chromatography-tandem mass spectrometry (LC-MS/MS), and electrochemiluminescence or electrogenerated.

Embodiments of the invention also provide treatment protocols based on the level of free testosterone, (SHBG)-bound testosterone, or non-SHBG, albumin-bound testosterone (non-SHBG-AT) measured using the methods of the invention. For example, if the level of free testosterone (FT) is low, the subject is administered a therapeutically effective amount of testosterone or if the level of free testosterone (FT) is high, the subject is administered a therapeutically effective amount of an agent that blocks testosterone. There are several exogenously applied testosterone products known in the art. The term "low" may refer to the lowest quarter of a population and the term high may refer to the highest quarter of a population. An exemplary testosterone blocker is Lupron.

In an alternative embodiment, if the level of (SHBG)-bound testosterone (SHBG-T) or non-SHBG, albumin-bound testosterone (non-SHBG-AT) is high, the subject is administered a therapeutically effective amount of testosterone or if the level of (SHBG)-bound testosterone (SHBG-T) or non-SHBG, albumin-bound testosterone (non-SHBG-AT) is low, the subject is administered a therapeutically effective amount of an agent that blocks testosterone. For example, in the case of women with PCOS who have low SHBG and high testosterone, giving insulin sensitizers like metformin to improve insulin resistance which will raise the level of SHBG in turn decreasing the level of bioavailable testosterone.

Embodiments of the invention also provided a method for predicting susceptibility or likelihood of a subject to develop cardiodiabetes, cardiovascular disease, diabetes, fatty liver disease, and/or metabolic syndrome in a subject, comprising:
  a) measuring levels of total testosterone (TT), SHBG-bound testosterone (SHBG-T), non-SHBG, albumin-bound testosterone (non-SHBG-AT) and/or free testosterone (FT) in a biological sample of the subject;
  b) comparing the levels of total testosterone (TT), SHBG-bound testosterone (SHBG-T), non-SHBG, albumin-bound testosterone (non-SHBG-AT) and/or free testosterone (FT) with a reference level of each corresponding total testosterone (TT), SHBG-bound testosterone (SHBG-T), non-SHBG, albumin-bound testosterone (non-SHBG-AT) and/or free testosterone (FT); and
  c) assessing the susceptibility or likelihood of the subject to develop cardiodiabetes, cardiovascular disease, diabetes, fatty liver disease, and/or metabolic syndrome based on the comparison in (b), wherein a decreased level or a deficiency of total testosterone (TT), SHBG-bound testosterone (SHBG-T), non-SHBG, albumin-bound testosterone (non-SHBG-AT), and/or free testosterone (FT) indicates that the subject is susceptible to or has an increased likelihood of developing cardiodiabetes, cardiovascular disease, diabetes, fatty liver disease, and/or metabolic syndrome.

In some embodiments, this method further comprises effectuating a therapy guidance based on the assessment in (c) and an analysis whether the subject is at a low a moderate or a high risk of developing cardiodiabetes, cardiovascular disease, diabetes, fatty liver disease, and/or metabolic syndrome.

Another aspect of the invention provides a kit to carry out the methods of the invention. The kit may comprise a blood card as described herein and shown in FIG. 2 and optionally directions, a lancet, and a pre-paid mailing envelope. The blood card comprises one spot that is impregnated with aromatase and/or aromatase and a NADPH cofactor. As shown in FIG. 3, a biological sample can be contacted and placed into a tube for delivery to a diagnostic laboratory.

Figure 2:
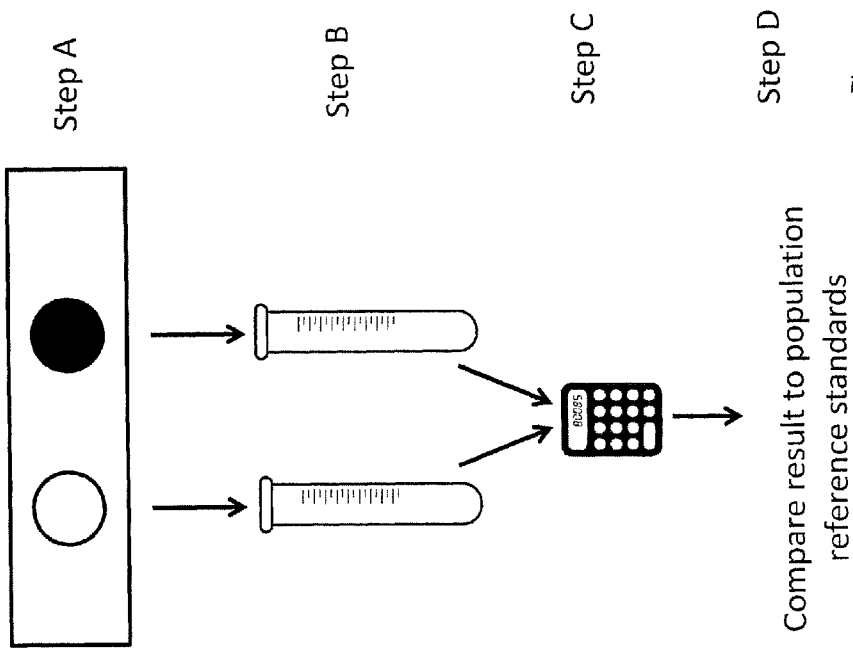
FIG. 2. An exemplary blood card of the invention.
Figure 3:
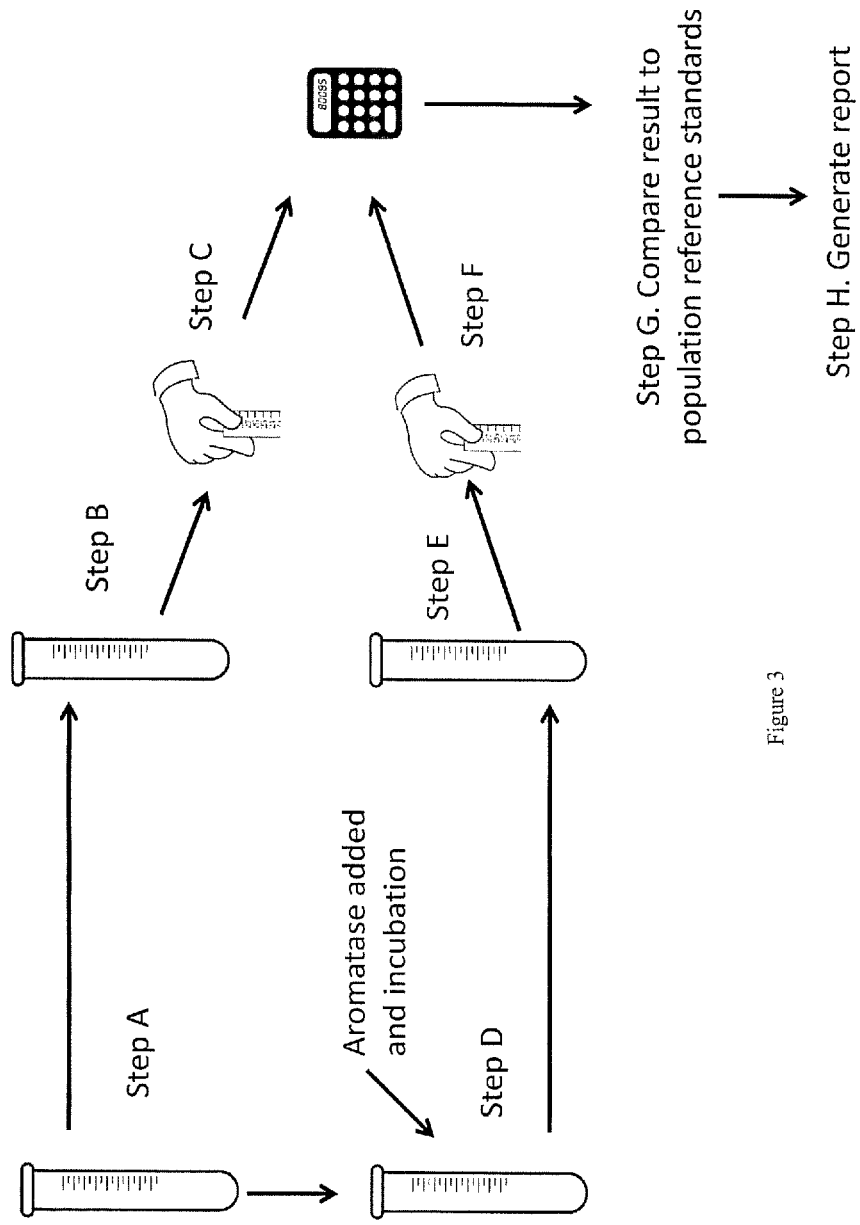
FIG. 3. An exemplary embodiment of the invention.

An exemplary embodiment of the invention is shown in FIG. 2. In step A, the patient or medical provider draws blood with a lancet, and a drop of blood is deposited onto each of two spots on an absorbant paper material (a blood card). The spot shown in white is a control spot with no chemicals applied and the spot shown in black has been pre-treated with aromatase enzyme. The blood is allowed to dry on the spots, and the card is mailed to the diagnostic laboratory. In step B, at the laboratory the blood spots are punched out or swabbed off and the blood is reconstituted/dissolved in appropriate buffers in two different tubes. Total testosterone and estradiol are measured for the first (control tube) and estradiol is measured from the second tube containing blood that had dried on the spot impregnated with aromatase enzyme. In step C, a computer system compares the amount of estradiol measured in the two samples, subtracting the lower amount in the first sample from the amount in the second sample. The difference is interpereted by the computer system as the amount of biologically active testosterone, and is reported in ng/mL. The computer further compares the amount of biologically active testosterone to total, and reports a value for total testosterone and a percentage of total testosterone that is biologically active. In step D, the computer further compares the amounts to reference ranges in a database for the appropriate age and sex of the patient and generates a report. The amount of biologically active testosterone, total testosterone, and percentage are reported out on the report as being within normal limits, high or low depending on the reference population. Based on the report, the physician makes treatment decisions regarding supplementation with exogenous testosterone, hormone blockers, insulin sensitizers, etc.

FIG. 3 illustrates another embodiment of the invention. In step A, a biological sample is contacted and placed into a tube for delivery to the diagnostic laboratory. In step B, a sample is extracted from the tube in A, and total testosterone and estradiol are measured via an assay known to those familiar with the art. In step C, the measurement of total testosterone and estradiol are stored in a computer system. In step D, aromatase enzyme is added to a sample of biological fluid from the original tube from step A; the aromatase is allowed to react for a period of time. In step E the amount of estradiol is measured after the aromatase reaction, and the result sent to the computer system in step F. In step G, the computer system compares the amount of estradiol measured in the two samples with an without aromatase enzyme, subtracting the measured amount in the first sample from the measured amount in the second sample. The difference is interpreted by the computer system as the amount of biologically active testosterone, and is reported in ng/mL. The computer further compares the amount of biologically active testosterone to total, and reports a value for total testosterone and a percentage of total testosterone that is biologically active. In step G, the computer further compares the amounts to reference ranges in a database for the appropriate age and sex of the patient and generates a report in step H. The amount of biologically active testosterone, total testosterone, and percentage are reported out on the report as being within normal limits, high or low depending on the reference population. Based on the report, the physician makes treatment decisions regarding supplementation with exogenous testosterone, hormone blockers, insulin sensitizers, etc.

Known ranges of testosterone relating to human health are broken down in the following table (Mayo Clinic, 2013)

Testosterone, Free
Males: 9-30 ng/dL
Females: 0.3-1.9 ng/dL
Reference values are not established for subjects <16 years.
Testosterone, Total
Males
0-5 months: 75-400 ng/dL
6 months-9 years: <7-20 ng/dL
10-11 years: <7-130 ng/dL
12-13 years: <7-800 ng/dL
14 years: <7-1,200 ng/dL
15-16 years: 100-1,200 ng/dL
17-18 years: 300-1,200 ng/dL
> or =19 years: 240-950 ng/dL
Tanner Stages*
I (prepubertal): <7-20
II: 8-66
III: 26-800
IV: 85-1,200
V (young adult): 300-950
Females
0-5 months: 20-80 ng/dL
6 months-9 years: <7-20 ng/dL
10-11 years: <7-44 ng/dL
12-16 years: <7-75 ng/dL
17-18 years: 20-75 ng/dL
> or =19 years: 8-60 ng/dL
Tanner Stages*
I (prepubertal): <7-20
II: <7-47
III: 17-75
IV: 20-75
V (young adult): 12-60

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1

A 25 year old woman is suspected of having PCOS by her clinician due to physical characteristics such as weight gain, increased amount of acne, and difficulty getting pregnant. The woman has blood drawn and her total testosterone measured by conventional techniques and is told that her total testosterone is within normal limits (50 ng/dL) and the physician makes the decision not to treat the patient for PCOS. The same patient's blood is drawn and the invention described herein is used to measure her biologically active testosterone. First, testosterone total and estradiol are measured, then, aromatase is added to the sample. The aromatase is given time to react with the free testosterone, converting it to estradiol. The estradiol level is measured again. In a computer system, the amount of estradiol in the first measurement is subtracted from the amount in the second measurement. The difference is equivalent to the amount of free testosterone that was present and available to react with the aromatase. The computer system then calculates the absolute amount of biologically active testosterone, and also compares this amount to the total testosterone from the first measurement, performing a calculation to yield the percent of biologically active testosterone. The results are reported to the physician. The physician notices that while the total amount of testosterone in the patient's blood was within normal limits, the absolute amount of biologically active testosterone and the percentage of total testosterone that was biologically active was abnormally high. The physician, as a result of this improved assay, makes a different treatment decision. She decides to treat the patient with Metformin to improve insulin resistance which in many cases will also raise the level of SHBG in PCOS patients, bringing their hormones back into balance. Months later, the patient returns to the doctor. The doctor re-runs both tests. The conventional test shows total testosterone within normal limits. The new invention described herein shows that the amount of biologically active testosterone has dropped in absolute amount and percentage. The physician concludes from the new improved test that the patient's hormonal imbalance as a result of her PCOS has improved, but still requires further treatment. The patient is prescribed a higher amount of Metformin and her symptoms are monitored and her biologically active testosterone is tested repeatedly to assess her health and response to treatment.

Example 2

A 45 year old man presents to his physician complaining of fatigue and low sex drive. He has seen commercials for testosterone replacement products for "low T" and demands that the doctor prescribe him this product. The doctor runs both a standard "total testosterone test" but also orders the test described herein to measure biologically active testosterone. The patient's total blood testosterone level is reported at 100 ng/dL which the physician considers equivocal. The biologically active testosterone is then measured on the patient's blood sample and reported as described above in example 1. The results of the new and improved test for biological activity shown herein show that the absolute amount of biologically active testosterone and the percentage of biologically active testosterone are well within normal limits for the man's age. As a result of the test described herein, the physician elects not to treat the patient with exogenously applied testosterone products, and to run additional tests to pinpoint the source of the patient's fatigue.

Example 3

A 45 year old man presents to his physician complaining of fatigue and low sex drive. He has seen commercials for testosterone replacement products for "low T" and demands that the doctor prescribe him this product. The doctor runs both a standard "total testosterone test" but also orders the test described herein to measure biologically active testosterone. The patient's total blood testosterone level is reported at 100 ng/dL which the physician considers equivocal. The biologically active testosterone is then measured on the patient's blood sample and reported as described above in example 1. The results of the new and improved test for biological activity shown herein show that the absolute amount of biologically active testosterone and the percentage of biologically active testosterone are below normal limits for the man's age. As a result of the test described herein, the physician elects to treat the patient with exogenously applied testosterone products.

Example 4

A fit 55 year old man is diagnosed with prostate cancer. His oncologist and urologist are concerned that the cancer may have micrometastasized and they know that prostate cancer grows in response to biologically active testosterone. The doctors decide to measure the amount of testosterone in his blood and run both a standard "total testosterone test" but also orders the test described herein to measure biologically active testosterone. The patient's total blood testosterone level is reported at 100 ng/dL which the physicians consider equivocal. The biologically active testosterone is then measured on the patient's blood sample and reported as described above in example 1. The results of the new and improved test for biological activity shown herein show that the absolute amount of biologically active testosterone and the percentage of biologically active testosterone are high for the man's age. As a result of the test described herein, the physicians elect to treat the patient with an agent that blocks the activity of or biological response to testosterone (like Lupron) in order to minimize the chances that the prostate cancer will recur.

The invention claimed is:

1. A method for measuring or determining a level of biologically active testosterone in a biological sample of a subject comprising:
   converting testosterone in said sample to a testosterone precursor by exposure of said sample to amoratase enzyme;
   detecting either said testosterone or said testosterone precursor in said sample before and after said converting step; and
   calculating biologically active testosterone in said sample from differences between either said testosterone or said testosterone precursor detected before and after said converting step.

2. The method of claim 1, wherein the biological sample is selected from the group consisting of serum, plasma and saliva.

3. A method for measuring or determining a level of biologically active testosterone in a biological sample of a subject, comprising:
   a) obtaining a first measurement of total testosterone for the biological sample; then
   b) adding an aromatase enzyme and a NADPH cofactor to the biological sample to facilitate an aromatase reaction with testosterone in the biological sample; then
   c) obtaining a second measurement of total testosterone for the biological sample after the aromatase reaction; and then
   d) calculating the level of the biologically active testosterone in the sample based on the difference between the first measurement and the second measurement of total testosterone.

4. The method of claim 3, wherein the biological sample is selected from the group consisting of serum, plasma and saliva.

* * * * *